US009609110B2

(12) United States Patent
Strom et al.

(10) Patent No.: US 9,609,110 B2
(45) Date of Patent: Mar. 28, 2017

(54) APPARATUS FOR BI-DIRECTIONAL COMMUNICATION WITH MEDICAL AND WELLNESS DEVICES

(71) Applicants: Adam Strom, San Antonio, TX (US); Mark Casillas, San Antonio, TX (US)

(72) Inventors: Adam Strom, San Antonio, TX (US); Mark Casillas, San Antonio, TX (US)

(73) Assignee: Mobius Connective Technologies, Ltd., San Antonio, TX (US)

( * ) Notice: Subject to any disclaimer, the term of this patent is extended or adjusted under 35 U.S.C. 154(b) by 0 days.

(21) Appl. No.: 14/159,486

(22) Filed: Jan. 21, 2014

(65) Prior Publication Data

US 2014/0206281 A1    Jul. 24, 2014

Related U.S. Application Data

(60) Provisional application No. 61/755,182, filed on Jan. 22, 2013.

(51) Int. Cl.
*H04M 1/725* (2006.01)
*G06F 19/00* (2011.01)

(52) U.S. Cl.
CPC .... *H04M 1/72527* (2013.01); *G06F 19/3418* (2013.01)

(58) Field of Classification Search
CPC .................................................. G06F 19/3418
See application file for complete search history.

(56) References Cited

U.S. PATENT DOCUMENTS

| 8,244,179 B2* | 8/2012 | Dua ............................ 455/41.2 |
| 2010/0217803 A1* | 8/2010 | Biondi et al. ................. 709/204 |
| 2012/0239407 A1* | 9/2012 | Lynch ............... G06Q 30/0201 704/500 |
| 2013/0058406 A1* | 3/2013 | Ye et al. ................... 375/240.12 |

* cited by examiner

*Primary Examiner* — Tuan H Nguyen
(74) *Attorney, Agent, or Firm* — Daniel A. Rogers; William H. Quirk; Rosenthal Pauerstein Sandoloski Agather LLP

(57) ABSTRACT

An apparatus that can communicate with multiple medical and/or wellness devices and encode data for efficient transmission is described. The apparatus can detect the presence of and receive data from one or more medical and/or wellness devices. The apparatus can receive, decode, store, process, encode, and forward received data through a wired and/or wireless interface. The wired data interface utilizes encoding techniques to render the data stream compatible with audio inputs of personal computing and communication devices.

12 Claims, 2 Drawing Sheets

APPARATUS FOR BI-DIRECTIONAL COMMUNICATION WITH MEDICAL AND WELLNESS DEVICES

CLAIM OF PRIORITY TO PRIOR APPLICATION

This application claims the benefit of the filing date of U.S. Provisional Application Ser. No. 61/755,182, filed on Jan. 22, 2013, entitled "Apparatus for Bi-Directional Communication with Medical and Wellness Devices", the entire disclosure of which is hereby incorporated by reference into the present disclosure.

BACKGROUND OF THE INVENTION

1. Field of the Invention

The present invention is in the field of telemedical data transfer. The present invention is an apparatus for bi-directional communication with medical and/or wellness devices. The apparatus allows universal telemedical data transfer from any medical and/or wellness device to any computer device.

2. Description of Related Art

Today many patients in need of medical services are enduring increasingly long waits in crowded emergency and waiting rooms. Even for routine examinations, it is not uncommon for patients to face long delays before meeting with their primary care provider. Furthermore, medical providers are often overbooked and cannot devote the time to their patients that once was common. Additionally, the costs of providing medical services have and continue to rise.

These factors have put pressure on medical service providers to find ways to streamline and enhance their medical practices. The medical field has adopted many technological devices to help in gathering the necessary data to provide correct medical diagnosis while maintaining an efficient and profitable practice. Some of these enhanced devices include stethoscopes, otoscopes, blood pressure cuffs, wearable thermometers, pulse oximeters, electrocardiograms, glucose monitors, and more. What these enhanced devices have in common is the electronic collection of medical vital signs and other data that is used by the medical professional to quickly and correctly identify medical issues for treatment. The idea is that by collecting the data electronically, wait times will be reduce, while also allowing medical providers to become more profitable.

However, with the proliferation of these data-gathering devices, medical professionals are discovering a new problem. That problem is how to efficiently gather and use the data produced from a myriad of incompatible medical devices. It is not uncommon for a medical practice to have high-tech equipment that employs a nurse to tediously and manually transfer the data generated using low-tech means such as pen and paper. So while the development of high-tech medical and wellness device had the goal of a more efficient and profitable practice, it oftentimes has resulted in additional labor and time to utilize the information generated.

Therefore, there is a long-felt need in the art for a universal, reliable, and consistent device and method to communicate with multiple medical and/or wellness devices and encode the data for efficient transmission.

SUMMARY OF THE INVENTION

The present invention is a universal device that communicates with multiple medical and/or wellness devices and encodes the data for efficient transmission. The apparatus can detect the presence of and receive data from one or more medical and/or wellness devices. The apparatus can receive, decode, store, process, encode, and forward received data through wired and/or wireless interfaces. The wired data interface utilizes encoding techniques to render the data stream compatible with audio inputs of personal computing and communication devices. The present invention answers a long-felt need in the art.

Many other objects, features, advantages, benefits, improvements and non-obvious unique aspects of the present invention, as well as the prior problems, obstacles, limitations and challenges that are addressed, will be evident to the reader who is skilled in the art, particularly when this application is considered in light of the prior art. It is intended that such objects, features, advantages, benefits, improvements and non-obvious unique aspects are within the scope of the present invention; the scope of which is limited only by the claims of this and any related patent applications and any amendments thereto.

To the accomplishment of all the above, it should be recognized that this invention may be embodied in the form illustrated in the accompanying drawings, with attention being called to the fact, however, that the drawings are illustrative only, and that changes may be made in the specifics illustrated or described.

BRIEF DESCRIPTION OF THE DRAWINGS

A better understanding of the invention for a universal and bi-directional device for communication with medical and wellness devices may be obtained from the drawings as described in greater detail in the DETAILED DESCRIPTION OF PREFERRED EMBODIMENT section which follows.

DETAILED DESCRIPTION OF PREFERRED EMBODIMENT

Figure 2:
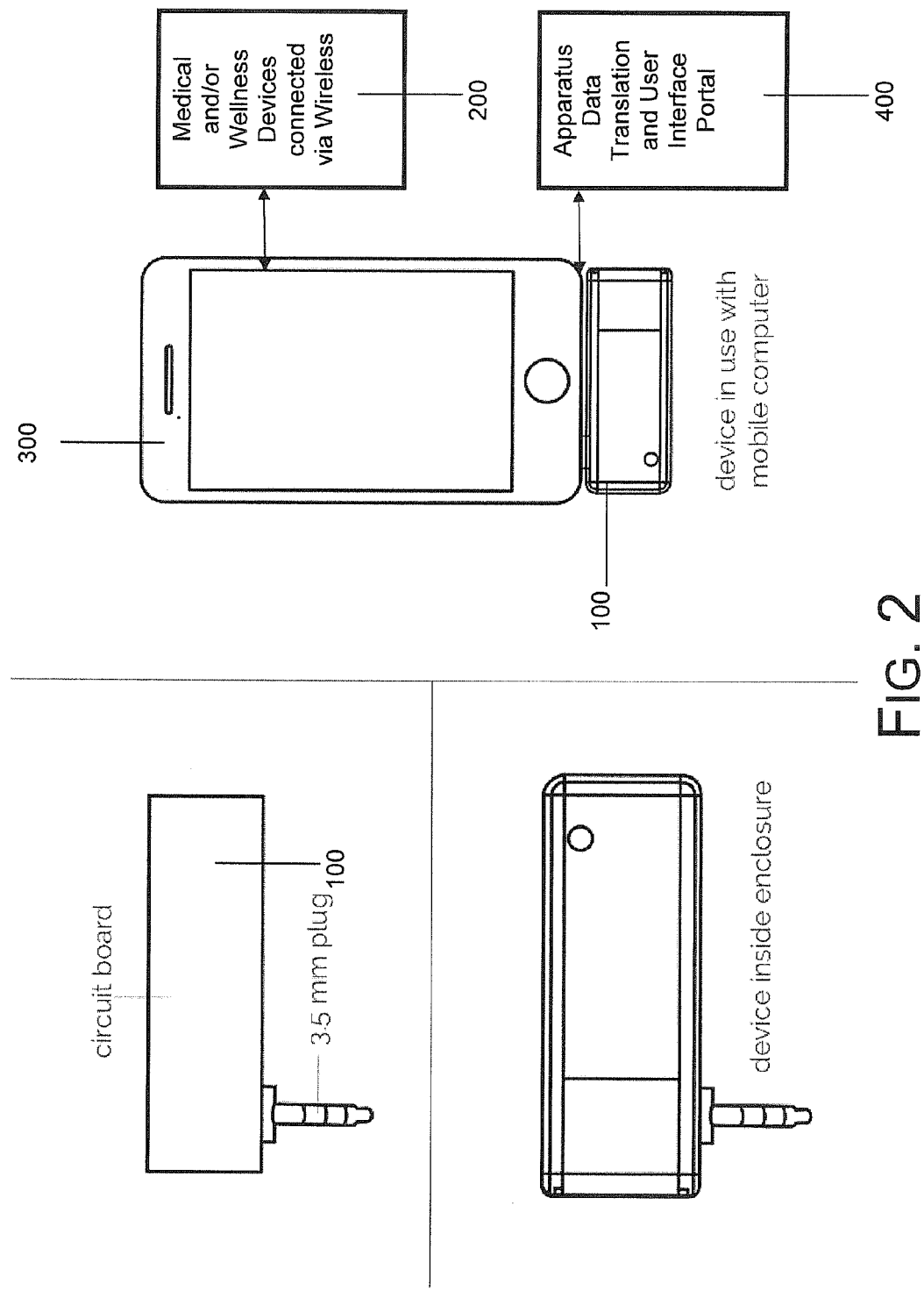
FIG. 2 is an overview of the major components of the Apparatus 100 of the invention and how the Apparatus 100 interfaces with the Personal Computing Device 200, the Medical and/or Wellness Device 300, and the Apparatus Data Translation and User Interface Portal 400.

FIG. 2 provides an overview of the invention and how it interfaces with current devices. The Apparatus 100 interfaces with the Personal Computing Device 200 and the Medical and/or Wellness Device 300. In FIG. 2 the Apparatus 100 is shown interfacing with the Personal Computing Device 200 via the audio interface 101 described in further details below and with the Medical and/or Wellness Device 300 via a wireless interface. It should be understood, however, that the actual interface between the Apparatus 100 and the Personal Computing Device 200 could be via a wireless connection. Likewise, the Apparatus 100 and the Medical and/or Wellness Device 300 could be interfaced via the audio interface 101. Finally, the Personal Computing Device 200 connects or runs the Apparatus Data Translation and User Interface Portal 400.

Figure 1:
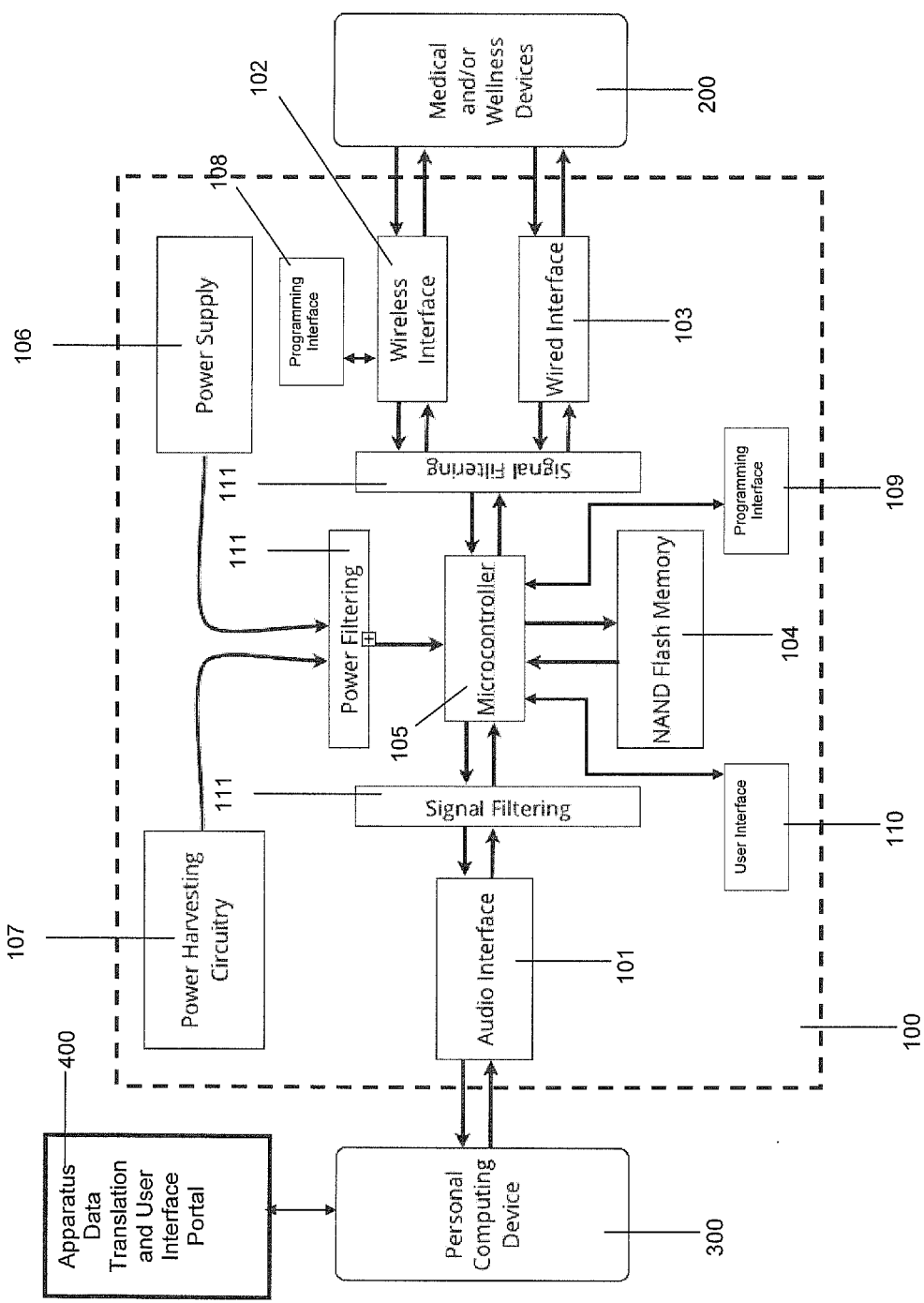
FIG. 1 is a detailed schematic of the components of the Apparatus 100 of the invention.

Turning to FIG. 1, which is a detailed schematic of the components of the Apparatus 100. The device contains the audio interface 101 between the described apparatus and the Personal Computing Device 200. In some alternatives, the audio interface 101 is between the described apparatus and the Medical and/or Wellness Device 300. The audio interface 101 uses a standard 3.5 mm headphone connection to transmit data to any computing device that has a 3.5 mm headphone jack. The microcontroller 105 interfaces with the other components of the device and translates the data received into an audio signal that passes to the audio interface 101 as an audio signal. This audio signal is received by the Personal Computing Device 200 and is then used by the Apparatus Data Translation and User Interface Portal 400.

The Apparatus Data Translation and User Interface Portal 400 serves as the main user interface of the invention. In the preferred embodiment, the Apparatus Data Translation and User Interface Portal 400 is a web application or website accessible via the internet or any network connection. In alternative embodiments, the Apparatus Data Translation and User Interface Portal 400 could be a program or application that runs on the Personal Computing Device 200 directly. The Apparatus Data Translation and User Interface Portal 400 translates and interprets the data collected and received from the Apparatus 100 and provides a user interface for accessing, storing, interpreting, and using the data.

The Apparatus 100 also contains one or more wireless interface 102 between the described apparatus and one or more Medical and/or Wellness Device 300. In addition to the wireless interface 102, the apparatus 100 contains one or more wired data interfaces 103 between the described apparatus and one or more Medical and/or Wellness Devices 300. The wired interface 103 may or may not receive or provide power to/from the Medical and/or Wellness Device 300 depending on the alternative embodiment. The wireless interface 102 could be any wireless interface such as Bluetooth®, ZigBee®, WiFi®, or other wireless interfaces known in the art. The wired data interface 103 could be any wired interface such as USB® or other wired interfaces known in the art.

The wireless interface 102 and wired interface 103 connected to one or more Medical and/or Wellness Device 300 and transmit the data received to the microcontroller 105. The microcontroller 105 is equipped with access to one or more of the NAND flash memory 104 units. NAND flash memory 104 units are used by the microcontroller 105 for storing temporary variables, received data, machine code, and/or other code necessary for apparatus function. Furthermore, some embodiments of the Apparatus 100 may contain a single microcontroller 105 or more. The microcontroller 105 is programmable and updatable. This allows the Apparatus 100 to receive firmware updates to enable interoperability with newly-developed Personal Computing Devices 200 or Medical and/or Wellness Devices 300.

The Apparatus 100 also contains supporting power circuitry for providing power to the apparatus from a direct current source such as a battery or solar cell, the power supply 106. In the preferred embodiment, the Apparatus 100 additionally includes supporting power harvesting circuitry that has an input of a sound wave and one or more outputs of a direct current voltage(s) for purposes of providing power to the apparatus, the power harvesting circuitry 107.

In FIG. 2, the programming interface 108 is depicted as connected via the wireless interface 102. In alternative embodiments, the programming interface 108 may be connected to other interfaces such as the audio interface 101, the wireless interface 102, and/or the wired interface 103. The programming interface 108 is used for firmware upgrades of the wireless stack.

As stated previously, the microcontroller 105 is programmable. In FIG. 2, the programming interface 109 is depicted as connected to the microcontroller 105. In alternative embodiments, the programming interface 108 may be connected to other interfaces such as the audio interface 101, the wireless interface 102, and/or the wired interface 103. The programming interface 109 is used for firmware upgrades of the machine code of the microcontroller 105, and for updating any other software and/or firmware components of the Apparatus 100.

In some alternatives, the Apparatus 100 contains the user interface 110 such as liquid crystal displays or light emitting diodes indicating the current functioning status of the apparatus and/or connected devices and/or the apparatus power supply. Additionally, the Apparatus 100 contains the signal filtering 111 on all interfaces, audio interface 101, the wireless interface 102, and/or the wired interface 103, to minimize electromagnetic interference.

The Apparatus 100 has several operating modes as described below. Normal operating mode is where data are transmitted in near real-time from the connected Medical and/or Wellness Device 300 to the connected Personal Computing Device 200. Low energy receiving mode is to save power while the Apparatus 100 is not connected to a Personal Computing Device 200 but is still receiving data from Medical and/or Wellness Device 300 connected to the audio interface 101, the wireless interface 102, and/or the wired interface 103. In this case, the microcontroller 105 data stores the data in the on-board NAND flash memory 104. Data storage retrieval mode is where the microcontroller 105 transmits data from the on-board NAND flash memory 104 contained within the Apparatus 100 to a connected Personal Computing Device 200. Low energy sleep mode saves power while the Apparatus 100 is not connected to the Personal Computing Device 200 through the audio interface 101. Firmware upgrade mode allows the transmission of updated machine code to the onboard microcontroller 105 via the programmable interface 109.

The usage sequence of the preferred embodiment of the invention is described as follows:

1.) A supporting software application (also known as the Apparatus Data Translation and User Interface Portal 400) on the Personal Computing Device 200 initiates communication with the Apparatus 100.

2.) The Apparatus Data Translation and User Interface Portal 400 communicates with the Apparatus 100 indicating its current status and instruction set.

3.) The Apparatus 100 communicates the availability of Medical and/or Wellness Device 300 and their descriptors as well as other relevant information.

4.) The Apparatus Data Translation and User Interface Portal 400 communicates to the Apparatus 100 which Medical and/or Wellness Device 300 data it is prepared to receive.

5.) The Apparatus 100 communicates with Medical and/or Wellness Device 300 and begins to receive data.

6.) The Apparatus 100 formats the data into the appropriate packets (packetizing) that the Apparatus Data Translation and User Interface Portal 400 on the Personal Computing Device 200 expects.

7.) The Apparatus 100 encodes the data (using Manchester Encoding if transmission is via an audio interface as to not saturate the audio input of the connected Personal Computing Device) 200.

8.) The Apparatus 100 outputs the data through the audio interface 101.

9.) The Apparatus Data Translation and User Interface Portal 400 regularly acknowledges the receipt of data and communicates further instructions to the Apparatus 100 regarding data transmission.

In some embodiments of the present invention, the method and systems described are provided via computer software, either via the internet, via a stand-alone software application operating independently or in connection with other software systems, or some combination of the two. As well, embodiments may come in any known form and may also be implemented by hardware, software, scripting languages, firmware, middleware, microcode, hardware description languages, and/or any combination thereof.

When implemented with coded programming, it should also be understood that the program code or code segments to perform the necessary steps or tasks of alternative embodiments may be coded in solid state or may be stored in a machine-readable medium such as a computer storage medium. A code segment or machine-executable step or instruction may represent a procedure, a function, a subprogram, a program, a routine, a subroutine, a module, a software package, a script, a class, or any combination of instructions, data structures, and/or program statements. Executable code segments may also be coupled to other code segments or to a hardware circuit by passing and/or receiving information, data, arguments, parameters, and/or memory contents, which may be passed, forwarded, or transmitted via any suitable means including memory sharing, message passing, token passing, network transmission, etc.

With reference again to the figures, it should be understood that the graphical representation of the system is an exemplary reference to any number of software, hardware, and business systems that may be implemented by the present invention whether through the web or as a stand-alone executable.

Specific details are given in the above description to provide a thorough understanding of various preferred embodiments. However, it is understood that these and other embodiments may be practiced without these specific details. For example, processes may be shown in diagrams in order not to obscure the embodiments in unnecessary detail. In other instances, well-known processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, or other electronic units designed to perform the functions described above, and/or a combination thereof.

Also, it is noted that the embodiments may be described as a process that is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed but could have many additional steps not included in the figure. A process may correspond to a method, a function, a procedure, a subroutine, a subprogram, etc. When a process corresponds to a function, its termination corresponds to a return of the function to the calling function or the main function.

Embodiments of the invention may involve middleware and/or other software implementations; the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may be downloadable through an internet connection service. As used herein, the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read-only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to portable or fixed storage devices, optical storage devices, wireless channels, and/or various other storage mediums capable of storing that contain or carry instruction(s) and/or data.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

While the principles of the disclosure have been described above in connection with specific methods, it is to be clearly understood that this description is made only by way of example and not as limitation on the scope of the disclosure. Whether now known or later discovered, there are countless other alternatives, variations and modifications of the many features of the various described and illustrated embodiments, both in the process and in the system characteristics, that will be evident to those of skill in the art after careful and discerning review of the foregoing descriptions, particularly if they are also able to review all of the various systems and methods that have been tried in the public domain or otherwise described in the prior art. All such alternatives, variations and modifications are contemplated to fall within the scope of the present invention.

Although the present invention has been described in terms of the foregoing preferred and alternative embodiments, these descriptions and embodiments have been provided by way of explanation of examples only, in order to facilitate understanding of the present invention. As such, the descriptions and embodiments are not to be construed as limiting the present invention, the scope of which is limited only by the claims of this and any related patent applications and any amendments thereto.

The invention claimed is:

1. A device for communicating with one or more medical devices and encoding data for efficient transmission, comprising:
    a) an audio encoded data interface that connects with an audio port of a personal computing device;
    b) a wireless interface;
    c) a microcontroller that encodes the medical device data into an audio format;
    d) wherein said microcontroller communicates data with the one or more medical devices via said audio encoded data interface or the wireless interface;
    e) further wherein said microcontroller communicates said medical device data with the personal computing device via said audio encoded data interface or the wireless interface; and
    f) wherein said personal computing device transmits audio formatted medical device data into an internet accessible database.

2. A communication and audio data encoding system comprising:
    a) a communication interface of a personal computing device for communicating with one or more medical devices;
    b) the communication interface for communicating with an internet accessible database;
    c) a programmable microcontroller of the personal computing device for encoding data in audio format from said one or more medical devices through said communication interface;
    and d) wherein said communication interface transmits audio formatted medical device data into the internet accessible database.

3. The system of claim 2 also comprising a user interface for displaying information regarding the function of said medical device.

4. The system of claim 2 also comprising a memory unit for storing data.

5. The system of claim 2 wherein said medical device communication interface is audio.

6. The system of claim 2 wherein said medical device communication interface is wireless.

7. The system of claim 2 wherein said medical device communication interface is wired.

8. The system of claim 2 wherein said personal computing communication interface is audio.

9. The system of claim 2 wherein said personal computing communication interface is wireless.

10. The system of claim 2 wherein said personal computing communication interface is wired.

11. The system of claim 2 wherein said medical device communication interface and said personal computing communication interface is the same interface.

12. A method of distributing medical device data over a network to a remote subscriber computer, the method comprising:
    a) providing a medical device data translation and user interface portal to a subscriber for access on the remote subscriber computer; wherein the medical device data translation and user interface portal being configurable by the subscriber allowing for customized accessing, storing, interpreting, and using the medical device data;
    b) providing a data collection user interface to the subscriber for use on a personal computer device;
    c) providing an apparatus to the subscriber for use with the personal computer device and one or more medical devices;
    d) receiving the medical device data at the personal computer device via the apparatus;
    e) wherein the personal computer device receives an audio formatted medical device data and transmits the medical device data over an internet via the data collection user interface; and
    f) wherein the medical device data is available to the subscriber for access on the remote subscriber computer via the medical device data translation and user interface portal.

* * * * *